(12) United States Patent
Allegretto et al.

(10) Patent No.: US 6,218,430 B1
(45) Date of Patent: *Apr. 17, 2001

(54) VITAMIN $D_3$ MIMICS

(75) Inventors: Elizabeth A. Allegretto, La Jolla; Marcus F. Boehm; Alex M. Nadzan, both of San Diego, all of CA (US)

(73) Assignee: Ligand Pharmaceuticals Incorporated, San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 48 days.

(21) Appl. No.: 09/139,040

(22) Filed: Aug. 24, 1998

(51) Int. Cl.$^7$ ................................. A61K 31/336
(52) U.S. Cl. ................ 514/475; 514/741; 548/961; 549/516; 549/545; 568/715
(58) Field of Search .................. 549/516, 545; 568/722, 728, 715; 548/954, 961, 969; 514/475, 741

(56) References Cited

U.S. PATENT DOCUMENTS

| | | | |
|---|---|---|---|
| 3,298,998 | 1/1967 | McConnell et al. | 260/47 |
| 3,410,825 | 11/1968 | Coover, Jr. et al. | 260/47 |
| 4,093,555 | 6/1978 | Schmitt et al. | 252/188 |
| 4,983,191 | * 1/1991 | Ekiner et al. | 55/158 |
| 5,128,491 | 7/1992 | Cheng | 549/516 |
| 5,190,935 | 3/1993 | Binderup et al. | 514/167 |
| 5,334,772 | 8/1994 | Plotkin et al. | 568/609 |

FOREIGN PATENT DOCUMENTS

| | | | |
|---|---|---|---|
| 145895 | 1/1967 | (CH) . | |
| 1 489 659 | 2/1975 | (GB) | 403/12 |

OTHER PUBLICATIONS

Saporito et al. 1994; M.S., Saporito et al. Exp. Neurol, 1993, 123, 295–302.
S. Carswall, abstract IBC Conference, "The Potential of Vitamin D Analogs for the Alzheimer's Disease"; Philadelphia, PA 1997.
M. Haq et al. J. Clin. Invest. 1993, 91, 2416–2422; K. Endo et al. J. Biol. Chem. 32693–32699.
E.L. Smith et al. J. Amer. Acad. Dermatol, 1988, 19, 516–528.
R. Bouillon et al. Endrocrine Rev. 1995, 16, 200–257.
K. Kragballe et al. Br. J. Dermatol, 1988, 119, 223–230.
H.H. Garcher et al. Asian J. Chem. 1993, 5, 340–347.
H.H. Garchar et al. Indian J. Pharm. Sci, 1993, 55, 141–144.
A.L. Cupples et al Epoxy Resins, Advances in Chemistry Series, 92 Chapter 15. American Chemical Society; Washington, DC, 1970, pp. 173–207.
I. Lerke et al. J. Appl. Polym. Sci. 1977, 21(8), 2067–2075.
I. Lerke et al. J. Appl. Polym. Sci. 1983, 28(2), 501–511.
I. Lerke et al. J. Appl. Polym. Sci. 1983, 28(2), 513,518.
S. Fregert et al., Contact Dermatitis 1984, 10(1), 47–48.
N.S. Dokhturishvili Chem. Abstracts 1977, 87:136690a.
G.Sh. Papava Chem. Abstracts 1986, 104:6199j.
M.F. Sorokin et al. Chem. Abstracts 1985, 102:63647m.
Z.L. Zarkua et al. Chem. Abstracts 1986, 105:225929W.
C.S. Kazakova et al. Chem. Abstracts 1984, 101:191261x.
K. Endo et al., J. Biol, Chem, 1994, 269, 32693–32699.

* cited by examiner

Primary Examiner—Sreeni Padmanabhan

(57) ABSTRACT

The present invention relates to non-secosteroidal compounds which activate and modulate the vitamin D receptor (VDR). Because compounds of the present invention display many of the beneficial properties of $1,25(OH)_2D_3$, but with reduced calcium mobilization effects, they may be used advantageously to treat and prevent conditions that show vitamin D sensitivity. Such disease states typically show abnormal calcium regulatory, abnormal immune responsive, hyperproliferative, and/or neurodegenerative characteristics.

38 Claims, 2 Drawing Sheets

*Fig. 3*

# VITAMIN D₃ MIMICS

FIELD OF THE INVENTION

In one aspect, the present invention relates to the synthesis of non-secosteroidal compounds having vitamin $D_3$ receptor (VDR) modulating activity. In another aspect, the invention relates to non-secosteroidal compounds, their pharmacologically acceptable salts, and pharmacologically acceptable compositions thereof which display VDR modulating activity in vitro and in vivo in mammals. In yet another aspect, the invention relates to methods of treating and preventing disease states in mammals with abnormal calcium regulatory, abnormal immune responsive, hyperproliferative, and/or neurodegenerative characteristics.

BACKGROUND AND PRIOR ART

The active form of vitamin $D_3$, 1,25-dihydroxyvitamin $D_3$ [$1,25(OH)_2D_3$], is a secosteroid long recognized as a major regulator of calcium homeostasis, and bone development and remodeling (M. R. Haussler et al. *N. Engl. J. Med.* 1977, 297, 974–983; H. F. DeLuca *FASEB J.* 1988, 2, 224–236). Work begun in the early 1980's has found that $1,25(OH)_2D_3$ is a potent differentiator of leukemic cells (E. Abe et al. *Proc. Natl. Acad. Sci.* 1981, 76, 4990–4994; S. Dokoh et al. *Cancer Res.* 1984, 44, 2103–2109; D. J. Mangelsdorf et al.*J. Cell. Biol.* 1984, 98, 391–398), as well as a growth inhibitor for cells of cancers such as prostate, breast, and colon (K. Colston et al. Endocrinology 1981, 108, 1083–1086; D. Bar-Shavitz et al. *Proc. Natl. Acad. Sci.* 1983, 80, 5907–591 1; R. J. Skowronski et al. *Endocrinology* 1993, 13Z 1952–1960). Immunosuppressive effects of $1,25(OH)_2D_3$ have been observed in vitro (D. D. Tsoukas et al. *Science* 1984, 224, 1438–1440; S. C. Manolagas et al. *Mol. Cell. Endocrinol.* 1985, 43, 113–122), and in animal models of lupus, diabetes, multiple sclerosis and rheumatoid arthritis (C. Mathieu et al. *Endocrinology* 1995, 136, 866–872; J. M. Lemire et al. *Autoimmunity* 1992, 12, 143–148; M. T. Cantora et al. *Proc. Natl. Acad. Sci.* 1996, 93, 7861–7864; M. T. Cantora et al. *J. Nutrition* 1998, 128, 68–72).

Declining levels of nerve growth factor (NGF) in old age is hypothesized to have a role in neurodegeneration and Alzheimer's disease. VDR is located in the areas of the brain where NGF is produced and where neurodegeneration is thought to occur (hippocampus and basal forebrain). 1,25 $(OH)_2D_3$ induces NGF in vitro in cell culture (M. S. Saporito et al. *Brain Res.* 1994, 633, 189–196; I. Neveu et al. Brain Res. *Mol. Brain Res.* 1994, 24, 70–76) and in vivo in the rat hippocampus and cortex (Saporito et al. 1994; M. S. Saporito et al. *Exp. Neurol.* 1993, 123, 295–302). Additionally, there has been a report that a $1,25(OH)_2D_3$ analogue has efficacy in a rodent model of Alzheimer's Disease (S. Carswell, abstract, *IBC Conference*, "The Potential of Vitamin D Analogs for the Treatment of Alzheimer's Disease", Philadelphia, Pa., 1997).

$1,25(OH)_2D_3$ binds to its intracellular receptor, the VDR, with high affinity and specificity resulting in transcriptional activation of vitamin D target genes such as those for the bone proteins osteocalcin and osteopontin. The $1,25(OH)_2 D_3$-VDR complex also regulates a key metabolic enzyme of $25(OH)D_3$ and $1,25(OH)_2D_3$, 25-hydroxyvitamin $D_3$-24-hydroxylase. Activation in these cases occurs through receptor binding to discrete regulatory regions within the promoters of these genes. VDR has been shown to form a heterodimer with the retinoid X receptor (RXR); this heterodimer binds with high affinity to vitamin D responsive elements (VDRE's) in the regulatory regions of the target genes (M. R. Haussler *Ann. Rev. Nutr.* 1986, 6, 527–562; K. Ozono *J. Bone Min. Res.* 1991, 6, 1021–1027).

Because in vitro (G. Zugmaier et al. Br. *J. Cancer* 1996, 73, 1341–1346; Y. Higashimoto et al. *Anticancer Res.* 1996, 16, 2653–2660; S. E. Blutt et al. *Endocrinology* 1997, 138, 1491–1497) and animal model (Y. Honma et al. *Cell Biol.* 1983, 80, 201–204; G. K. Potter et al. *Exp. Hematol.* 1985, 13, 722–732; K. W. Colston et al. *Biochem. Pharmacol.* 1992, 44, 693–702; J. A. Eisman et al. *Cancer Res.* 1987,47, 21–25; A. Belleli et al. *Carcinogenesis* 1992, 13, 2293–2298) studies show $1,25(OH)_2D_3$ an effective agent in inhibiting growth and inducing differentiation of a variety of cancer types, this compound is a potential drug for treatment of these conditions in humans. $1,25(OH)_2D_3$ analogs also have shown effectiveness in animal models of humoral hypercalcemia of malignancy (HHM) (M. Haq et al.*J. Clin. Invest.* 1993, 91, 2416–2422; K. Endo et al. *J. Biol. Chem.* 1994, 269, 32693–32699).

$1,25(OH)_2D_3$ has demonstrated efficacy in the treatment of dermatological conditions. Analogs of $1,25(OH)_2D_3$ are effective treatments for psoriasis, a condition with both hyperproliferative and autoimmune components (E. L. Smith et al. *J. Amer. Acad. Dermatol.* 1988, 19, 516–528) and may also be effective in the treatment of other skin disorders including acne and wrinkles (E. T. Binderup et al. U.S. Pat. No. 5,190,935). $1,25(OH)_2D_3$ has also shown efficacy in the prevention of chemotherapy-induced hair-loss (alopecia) (J. J. Jimenez et al. *Cancer Res.* 1992, 52, 5123; J. J. Jimenez et al. *Clin. Res.* 1994, 42, 128A; J. J. Jimenez et al. *Am. J. Med. Sci.* 1995, 310, 43).

Known activities of vitamin $D_3$ are not limited to the treatment and cure of disease states, but also includes chemoprevention: the prophylactic use for the prevention of said disease states (Prostate cancer: M. S. Lucia *Cancer Res.* 1995, 55, 5621–5627. Breast cancer: M. A. Anzano et al. *Cancer Res.* 1994, 54, 1653–1656. Autoimmune disease models: Mathieu et al. 1995; Lemire et al. 1992).

Currently, $1,25(OH)_2D_3$, as Rocaltrol® (Hoffinann-La Roche), is administered to kidney failure patients undergoing chronic kidney dialysis to treat hypocalcemia and the resultant metabolic bone disease. Although many patients experience no side effects from this treatment, its usefulness is limited because the normal calcium mobilization function of $1,25(OH)_2D_3$ increases with dosage resulting in hypercalcemia (elevated serum calcium) in animals and humans. This only known side effect of $1,25(OH)_2D_3$ may cause soft tissue calcification which can be life threatening. Recently, chemical modifications of $1,25(OH)_2D_3$ have yielded analogs with attenuated calcium mobilization effects (R. Bouillon et aL *Endocrine Rev.* 1995, 16, 200–257). One such analog, MC903 or Dovonex® (Bristol-Meyers Squibb), is currently used in Europe and the United States as a topical treatment for mild to moderate psoriasis (K. Kragballe et al. *Br. J. Dermatol.* 1988, 119, 223–230).

The therapeutic potential of $1,25(OH)_2D_3$ has spurred the development of secosteroidal analogs of $1,25(OH)_2D_3$ with reduced calcemic effects and that retain desirable properties, and in fact, all compounds previously known to activate the VDR are secosteroidal analogs of the parent $1,25(OH)_2D_3$. Although some degree of separation between the beneficial and calcium raising (calcemic) effects has been achieved in these analogs, to date the separation has been insufficient to allow for oral administration to treat conditions such as cancers, leukemias, and severe psoriasis.

Thus, the development of compounds in which the VDR modulating activity is more fully divorced from calcium mobilization activity might lead to effective treatments for disease states responsive to vitamin $D_3$ and its analogs including those with abnormal calcium regulatory, abnormal immune responsive, hyperproliferative, and/or neurodegenerative characteristics such as leukemia, cancers, psoriasis, renal osteodystrophy, renal failure, osteoporosis, humoral hypercalcemia of malignancy, acne, alopecia, host-graft rejection, lupus, multiple sclerosis, autoimmune induced diabetes, scleroderma, rheumatoid arthritis, acne, wrinkles, insufficient sebum secretion, insufficient dermal hydration, insufficient dermal firmness, and Alzheimer's disease.

BISPHENOLS

Bisphenols are a well-known family of compounds consisting of two phenol units, their para-positions geminally bonded to a bridging group such as an alkylidene, cycloalkylidene, sulfur atom, etc. These bisphenols and their derivatives are commonly used in polymers and as plasticizers.

Bisphenol-C and some derivatives have been screened for antimicrobial and antifungal activity; ring nitrated compounds had the highest antifungal activities (H. H. Garchar et al. *Asian J. Chem.* 1993, 5, 340–347). The antibacterial, antifungal, and hypotensive activities of some propanolamine-substituted bisphenol derivatives has also been studied (H. H. Garchar et al. *Indian J. Pharm. Sci.* 1993, 55, 141–144). Neither reference describes any VDR activity.

Derivatives of bisphenols are well known in the polymer arts. Bisglycidyl ethers of bisphenols have been particularly well studied as polymer precursors as described in U.S. Pat. Nos. 3,298,998 and 3,410,825, and Czechoslovak patent CS 145895 for the production of epoxy and polyether resins. U.S. Pat. No. 5,128,491 describes a method for the preparation of bisglycidyl ethers of substituted bisphenols with high monomer content. The syntheses and reactivities of a number bisglycidyl bisphenol ethers for rapid curing epoxy resins have been reported (A. L. Cupples et al. *Epoxy Resins, Advances in Chemistry Series*, 92 Chapter 15, American Chemical Society: Washington DC, 1970, pp 173–207). The effectiveness of a series of compounds including the bisglycidyl ether of 4,4'-isopropylidenedi(2-methylphenol) as stabilizers for γ-irradiated PVC has been reported in a series of articles (I. Lerke et al. *J. Appl. Polym. Sci.* 1977, 21(8), 2067–2075; I. Lerke et al. *J. Appl. Polym. Sci.* 1983, 28(2), 501–511; I. Lerke et al. *J. Appl. Polym. Sci.* 1983, 28(2), 513–518). A study of the sensitizing potential of a number of bisglycidyl bisphenol ethers has been performed (S. Fregert et al. *Contact Dermatitis* 1984, 10(1), 47–48). None of these references describes any VDR activity.

U.S. Pat. No. 4,093,555 and U.K. patent 1 489 659 describe bisaziridinyl derivatives of brominated bisphenols which are useful in the production of dental models and tooth replacement parts. U.S. Pat. No. 5,334,772 describes alkenyl ethers of bisphenols susceptible to cationic polymerization. These bisphenol patents do not disclose any VDR activity.

Russian workers have also been active in the syntheses of bisphenol derivatives as polymer precursors. Norbornylidene bridged derivatives have been converted to their bisglycidyl ethers (N. S. Dokhturishvili *Chem. Abstracts* 1977, 87:136680a) and bis(2-hydroxyethyl) ethers (G. Sh. Papava *Chem. Abstracts* 1986, 104:6199j). The bisglycidyl ethers of a series of bisphenols were used as epoxy resin precursors (M. F. Sorokin et al. *Chem. Abstracts* 1985, 102:63647m). Bis(2-hydroxyethyl) ethers of adamantylidene-bridged, substituted bisphenols were synthesized as potential plasticizers (Z. L. Zarkua et al. *Chem Abstracts* 1986, 105:225929w). Di(carboxymethyl)ethers of substituted bisphenols have been reported (G. S. Kazakova et al. *Chem. Abstracts* 1984, 101:191261x). None of these references discloses any VDR activity.

To the extent necessary to understand or complete the disclosure of the present invention, all cited patents and publications are expressly incorporated by reference as if said patents and publications were reproduced in their entirety herein.

BRIEF DESCRIPTION OF THE DRAWINGS

FIG. 1A shows that tumors (formed in nude mice by injection of LNCaP cells, vide infra) were smaller in mice at 10 and 15 days post dosing with compound 4 compared to mice receiving a vehicle. B: FIG. 1B shows that mice treated with compound 4 had normal serum calcium levels measured colorimetrically (Sigma Kit) at 10 and 15 days post dosing.

SUMMARY OF THE INVENTION

The present invention is directed towards non-secosteroidal compounds that bind to and activate the VDR, preferably without significant calcemic effects relative to $1,25(OH)_2D_3$. In one aspect, the present invention is directed to methods of modulating the VDR through the administration of compounds of the formula I:

wherein:
  X and Y are each independently selected from the group consisting of O, S, and $NR^7$;
  Z is selected from the group consisting of C=O, $CH(OR^8)$, and $CH(NR^9R^{10})$;
  $R^1$ and $R^2$ are independently selected from the group consisting of alkyl groups, optionally fluorinated; or together $R^1$ and $R^2$ form a cycloalkylidene having 3 to 8 carbon atoms, optionally fluorinated;
  $R^3$ and $R^4$ are independently selected from the group consisting of halogen; lower n-alkyl, optionally fluorinated; and lower alkoxy, optionally fluorinated;
  $R^5$ is selected from the group consisting of H; optionally substituted alkyl groups; optionally substituted alkenyl groups; optionally substituted alkynyl groups; optionally substituted aryl groups; $OR^{11}$; $NR^{12}R^{13}$; or together with $R^8$, $R^9$, or $R^{10}$ forms a 3- to 12-membered cyclic group wherein said cyclic group is selected from the group consisting of amidines, amines, ethers, lactams, lactones, ketals, hemiketals, aminals, hemiaminals, carbonates, carbamates, ureas, and combinations thereof;

$R^6$ is selected from the group consisting of H and alkyl groups, optionally substituted;

$R^7$ is selected from the group consisting of H and alkyl groups, optionally substituted;

$R^8$ is selected from the group consisting of H, optionally substituted alkyl groups, optionally substituted alkenyl groups, optionally substituted alkynyl groups, optionally substituted aryl group, and optionally substituted acyl groups;

$R^9$ and $R^{10}$ are independently selected from the group consisting of H, optionally substituted alkyl groups, optionally substituted alkenyl groups, optionally substituted alkynyl groups, optionally substituted aryl groups, and optionally substituted acyl groups;

$R^{11}$ is selected from the group consisting of H, optionally substituted alkyl groups, optionally substituted alkenyl groups, optionally substituted alkynyl groups, optionally substituted aryl groups, and optionally substituted acyl groups; and $R^{12}$ and $R^{13}$ are independently selected from the group consisting of H, optionally substituted alkyl groups, optionally substituted alkenyl groups, optionally substituted alkynyl groups, optionally substituted aryl groups, and optionally substituted acyl groups and pharmaceutically acceptable salts thereof.

In another aspect, the present invention relates to methods of treating disease states characterized by abnormal calcium regulation, cell proliferation, immune response, dermatological conditions and/or neurodegenerative conditions with compounds of formula I.

In the course of their research, the inventors have also discovered heretofore unknown non-secosteroidal compounds that bind to and modulate the activity of the VDR. Thus, in still another aspect, the present invention is directed to novel compounds of formula II:

II wherein:

X and Y are each independently selected from the group consisting of O, S, and $NR^7$;

Z is selected from the group consisting of C=O, CH(OR$^8$), and CH(NR$^9$R$^{10}$);

$R^1$ and $R^2$ are independently selected from the group consisting of alkyl groups, optionally fluorinated; or together $R^1$ and $R^2$ form a cycloalkylidene having 3 to 8 carbon atoms, optionally fluorinated;

$R^3$ and $R^4$ are independently selected from the group consisting of halogen; lower n-alkyl, optionally fluorinated; and lower alkoxy, optionally fluorinated;

$R^5$ is selected from the group consisting of H; optionally substituted alkyl groups; optionally substituted alkenyl groups; optionally substituted alkynyl groups; optionally substituted aryl groups; $OR^{11}$; $NR^{12}R^{13}$; or together with $R^8$, $R^9$, or $R^{10}$ forms a 3- to 12-membered cyclic group wherein said cyclic group is selected from the group consisting of amidines, amines, ethers, lactams, lactones, ketals, hemiketals, aminals, hemiaminals, carbonates, carbamates, ureas, and combinations thereof;

$R^6$ is selected from the group consisting of H and alkyl groups, optionally substituted;

$R^7$ is selected from the group consisting of H and alkyl groups, optionally substituted;

$R^8$ is selected from the group consisting of H, optionally substituted alkyl groups, optionally substituted alkenyl groups, optionally substituted alkynyl groups, optionally substituted aryl group, and optionally substituted acyl groups;

$R^9$ and $R^{10}$ are independently selected from the group consisting of H, optionally substituted alkyl groups, optionally substituted alkenyl groups, optionally substituted alkynyl groups, optionally substituted aryl groups, and optionally substituted acyl groups;

$R^{11}$ is selected from the group consisting of H, optionally substituted alkyl groups, optionally substituted alkenyl groups, optionally substituted alkynyl groups, optionally substituted aryl groups, and optionally substituted acyl groups; and $R^{12}$ and $R^{13}$ are independently selected from the group consisting of H, optionally substituted alkyl groups, optionally substituted alkenyl groups, optionally substituted alkynyl groups, optionally substituted aryl groups, and optionally substituted acyl groups and pharmaceutically acceptable salts thereof;

with the provisos that:
 a. when X and Y are both O, Z is C=O, and $R^5$ is selected from the group consisting of OH and $C_1$–$C_4$ alkoxy, then $R^6$ is not carboxymethyl and $C_1$–$C_4$ alkyl esters thereof;
 b. when X and Y are both O, and Z is selected from the group consisting of CH(OR$^8$) and CH(NR$^9$R$^{10}$), then $R^5$ is not H and primary alkyl;
 c. when X and Y are both O, and Z is CH(OR$^8$), then $R^6$ and $R^8$ do not both comprise aziridines;
 d. when X and Y are both O, and Z is CH(OR$^8$), then $R^5$, $R^6$, and $R^8$ do not simultaneously comprise alkenyl ethers; and
 e. when X and Y are both O, and Z is CH(OR$^8$), then $R^5$ and $R^6$ do not both comprise glycidyl ethers.

In another aspect, the present invention is directed towards pharmaceutical compositions containing pharmaceutically effective amounts of compounds of formulae I or II or pharmaceutically acceptable salts thereof, either singly or in combination, together with pharmaceutically acceptable carriers and/or auxiliary agents. Preparation of such compositions for topical, parenteral, and oral use as well as for unit dosage administration are well known in the pharmaceutical arts.

The present invention also relates to the use of these compositions to treat mammalian disease states. The inventors have discovered that compounds of formulae I and II display the desirable cell differentiation and antiproliferative effects of the active form of vitamin $D_3$, 1,25-dihydroxyvitamin $D_3$ [1,25(OH)$_2$D$_3$], with reduced calcium mobilization (calcemic) effects. Hence, these compositions may find use in the treatment and prevention (chemoprevention or prophylaxis) of disease states characterized by abnormal calcium regulation, cell proliferation, immune response, dermatological conditions, and/or neurodegenerative conditions.

DEFINITIONS

In accordance with the present invention and as used herein, the following terms are defined to have the following meanings, unless explicitly stated otherwise:

The term "acyl" refers to organic radicals —C(O)R, where R is H, aliphatic, or aromatic group; the attached group may be optionally substituted. Examples of acyl groups include acetyl and benzoyl groups. Suitable acyl groups have from 1 to about 20 carbon atoms.

The term "alkenyl" refers to aliphatic groups wherein the point of attachment is a carbon-carbon double bond, for example vinyl, 1-propenyl, and 1-cyclohexenyl. Alkenyl groups may be straight-chain, branched-chain, cyclic, or combinations thereof, and may be optionally substituted. Suitable alkenyl groups have from 2 to about 20 carbon atoms.

The terms "alkoxy" and "alkoxide" refer to —OR wherein R is an aliphatic or aromatic group which may be optionally substituted. Methoxy, ethoxy, and phenoxy are examples of alkoxy groups.

The term "alkyl" refers to saturated aliphatic groups including straight-chain, branched-chain, cyclic and any combinations thereof. Alkyl groups may further be divided into "primary", "secondary", and "tertiary" alkyl groups. In primary alkyl groups, the carbon atom of attachment is substituted with zero (methyl) or one organic radical. In secondary alkyl groups, the carbon atom of attachment is substituted with two organic radicals. In tertiary alkyl groups, the carbon atom of attachment is substituted with three organic radicals. Examples of alkyl groups include methyl, ethyl, cyclohexyl, allyl, benzyl, 7-norbornyl, and 3-pyrrolidinyl. Suitable alkyl groups have from 1 to about 20 carbon atoms, and may be optionally substituted.

The term "alkylidene" refers to geminal alkyl diradicals such as methylene, 2-propylidene, and cyclohexylidene.

The term "alkynyl" refers to aliphatic groups which have a carbon-carbon triple bond at the point of attachment, for example ethynyl. Alkynyl groups may comprise straight-chain, branched-chain, and/or cyclic portions, and may be optionally substituted. Suitable alkynyl groups have from 2 to about 20 carbon atoms.

The term "aliphatic" refers to organic compounds and radicals which may be straight-chain, branched-chain, non-aromatic cyclic, and combinations thereof. Aliphatic groups include alkyl, alkenyl, and alkynyl groups as well as their cyclic variants, and may be optionally substituted.

The term "amide" refers to derivatives of acids wherein one or more hydroxyl groups is replaced with a amino groups. The amino groups are optionally substituted with one or two organic radicals which may be aliphatic or aromatic. Arnides may be cyclic. The term "carboxamide" refers to an amide of a carboxylic acid. The term "aminocarbonyl" refers carboxamide radicals wherein the point of attachment is the carbonyl carbon. The term "acylamido" refers to carboxamide radicals wherein the point of attachment is the nitrogen atom. The term "amidine" refers to amides of imidic acids. The term "amidinyl" refers to amidine radicals of wherein the point of attachment is the required carbon atom.

The term "aminal" refers to derivatives of aldehydes or ketones wherein the carbonyl oxygen is replaced with two amino groups. Aminals may be cyclic.

The term "amine" refers to neutral trivalent nitrogen compounds comprising substituents independently selected from H and organic radicals with the proviso that none of the organic radicals are acyl groups. The term "amino" refers to nitrogen radicals derived from amines. Amines may be cyclic and cyclic amines may be aromatic. Examples of amines are triethylamine, morpholine, aniline, purine, and pyridine.

The terms "aryl" and "aromatic" refers to carbocyclic and heterocyclic compounds and radicals with conjugated pi-systems. Each aromatic nucleus typically comprises a 5- to 7-membered ring onto which additional aromatic nuclei may be fused. Aryl groups may be optionally substituted. Examples of aryl groups include are such as phenyl, naphthyl, furanyl, imidazolyl, and quinolinyl. Suitable aryl groups have from 5 to about 20 total carbon and heteroatoms.

The term "aziridine" refers to saturated, three-membered, cyclic monoamines.

The term "carbamate" refers to esters of carbamic acid wherein the amide nitrogen may also be substituted. Carbamates may be cyclic. An example of a carbamate is ethyl carbamate.

The term "carbocyclic" refers mono- and polycyclic compounds and radicals wherein the ring atoms are carbon atoms. Carbocyclic compounds may be aliphatic, aromatic, or combinations thereof. Examples of carbocyclic groups are phenanthryl, phenyl, cyclooctyl, norbornadienyl, acenaphthyl, and adamantyl.

The term "carbonate" refers to diesters of carbonic acid. Carbonates may be cyclic. Examples of carbonates include diethyl carbonate and propylene carbonate.

The terms "chemoprevention" and "chemopreventative" refer to the prophylactic use of an agent to prevent disease states and said agent, respectively.

The term "cycloalkylidene" refers to geminal cyclic alkyl diradicals such as cyclopropylidene, cyclopentylidene, cyclohexylidene, and cycloheptylidene which may be further alkyl substituted.

The term "DMF" refers to N,N-dimethylformamide.

The terms "epoxide" and "epoxy" refer to saturated, three-membered, cyclic monoethers.

The term "ester" refers to compounds wherein a hydroxy group of an acid is replaced with an alkoxide group. For example, a carboxylic ester is one in which the hydroxy group of a carboxylic acid is replaced with and alkoxide. Esters may derive from any acid comprising one or more hydroxy groups: for example, carbonic acid, carbamic acids, phosphonic acids, sulfonic acids, and boronic acids. The terms "alkoxycarbonyl" and "carboalkoxy" refer to carboxylic ester radicals wherein the point of attachment is the carbonyl carbon. The term "acyloxy" refers to carboxylic ester radicals wherein the point of attachment is the non-carbonyl oxygen atom.

The term "ether" refers to compounds wherein an oxygen atom is attached to two organic radicals with the proviso that neither organic radical is an acyl group. The term "oxa" also refers to ethers and indicates that the indicated carbon atom is replaced with an oxygen atom. Ethers may be cyclic. Examples of ethers include diethyl ether, morpholine, tetrahydrofuran, and ethylene oxide.

The term "glycidyl" refers to the 2,3-epoxypropyl group.

The terms "halogen" and "halo" refer to fluorine, chlorine, bromine, and iodine.

The term "hemiaminal" refers to derivatives of aldehydes or ketones wherein the carbonyl oxygen is replaced by an amino group and a hydroxy group. Hemiaminals may be cyclic.

The term "hemiketal" refers to derivatives of ketones wherein the carbonyl oxygen is replaced by an alkoxide and a hydroxide. Hemiketals may be cyclic. The term is used interchangeably with "hemiacetal" which is the corresponding derivative of an aldehyde.

The term "heterocyclic" refers to mono- and polycyclic compounds and radicals wherein the ring or rings comprise one or more heteroatoms. Suitable heteroatoms include oxygen, nitrogen, sulfur, phosphorus, and boron. Heterocyclic radicals may be attached at a carbon atom or heteroatom. Heterocyclic groups may be aliphatic, aromatic, or combinations thereof. Examples of heterocyclic groups are furanyl, epoxy, thiazolyl, pyrimidyl, imidazolyl, quinolinyl, indolinyl, quinuclidinyl, and morpholinyl.

The term "ketal" refers to derivatives of ketones wherein the carbonyl oxygen is replaced by two alkoxide groups. Ketals may be cyclic. The term is used interchangeably with "acetal" which is the corresponding derivative of an aldehyde.

The term "lactam" refers to cyclic carboxamides wherein the ring comprises both the carboxamide carbon and nitrogen atoms.

The term "lactone" refers to cyclic carboxylic esters wherein the ring comprises both the carbonyl carbon and non-carbonyl oxygen atom.

The term "lower" when modifying organic radicals refers to those organic radicals with up to and including 10, preferably up to and including six, and advantageously from one to four carbon atoms.

The terms "optionally substituted" and "substituted" indicate that the group in question is substituted with from one to about four independently selected conventional organic substituents such as acyl, acyloxy, alkenyl, alkoxy, alkoxycarbonyl, alkyl, alkynyl, amidinyl, amino, aminocarbonyl, aryl, azido, carboalkoxy, carboxamido, carboxy, cyano, epoxy, halo, hydroxy, nitro, oxa, oxo, perhaloalkyl, perhaloaryl, phosphino, phosphinyl, phosphonyl, sulfinyl, sulfonyl, thia, thio, and combinations and protected derivatives thereof.

The term "perhalo" when modifying an organic radical signifies that every hydrogen atom attached to a carbon atom is replaced with a halogen atom. "Perhalo" can modify both aliphatic and aromatic groups. Examples of perhaloalkyl groups are trifluoromethyl, bromodifluoromethyl, pentachloroethyl, and heptafluoroisopropyl. Examples of perhalo aromatic groups are tetrafluoro-4-iodophenyl and heptafluoro-2-naphthyl. The prefix "per" is often used instead of a numerical prefix when all of the halo groups are identical: for example, perfluoronaphthyl and perfluoroheptyl.

The term "pharmaceutically acceptable salt" includes salts of the compounds of the present invention derived from the combination of the compound and an organic or inorganic acid or base. In practice, acidic members of the compounds of formulae I and II would be combined with a base or bases, basic members of the compounds of formulae I and II would be combined with an acid or acids, and members of the compounds of formulae I and II with both acid and base finctionalities would be combined with one or more acids, bases or any combination thereof. Both the neutral and salt forms fall within the scope of the present invention.

The term "urea" refers to diamides of carbonic acid. Ureas may be cyclic. Urea is the prototypical urea.

DETAILED DESCRIPTION OF THE INVENTION

Compounds of the present invention with VDR modulating activities have formula I:

wherein:

X and Y are each independently selected from the group consisting of O, S, and $NR^7$;

Z is selected from the group consisting of C=O, $CH(OR^8)$, and $CH(NR^9R^{10})$;

$R^1$ and $R^2$ are independently selected from the group consisting of alkyl groups, optionally fluorinated; or together $R^1$ and $R^2$ form a cycloalkylidene having 3 to 8 carbon atoms, optionally fluorinated;

$R^3$ and $R^4$ are independently selected from the group consisting of halogen; lower n-alkyl, optionally fluorinated; and lower alkoxy, optionally fluorinated;

$R^5$ is selected from the group consisting of H; optionally substituted alkyl groups; optionally substituted alkenyl groups; optionally substituted alkynyl groups; optionally substituted aryl groups; $OR^{11}$; $NR^{12}R^{13}$; or together with $R^8$, $R^9$, or $R^{10}$ forms a 3- to 12-membered cyclic group wherein said cyclic group is selected from the group consisting of amidines, arnines, ethers, lactams, lactones, ketals, hemiketals, aminals, hemiaminals, carbonates, carbamates, ureas, and combinations thereof;

$R^6$ is selected from the group consisting of H and alkyl groups, optionally substituted;

$R^7$ is selected from the group consisting of H and alkyl groups, optionally substituted;

$R^8$ is selected from the group consisting of H, optionally substituted alkyl groups, optionally substituted alkenyl groups, optionally substituted alkynyl groups, optionally substituted aryl group, and optionally substituted acyl groups;

$R^9$ and $R^{10}$ are independently selected from the group consisting of H, optionally substituted alkyl groups, optionally substituted alkenyl groups, optionally substituted alkynyl groups, optionally substituted aryl groups, and optionally substituted acyl groups;

$R^{11}$ is selected from the group consisting of H, optionally substituted alkyl groups, optionally substituted alkenyl groups, optionally substituted alkynyl groups, optionally substituted aryl groups, and optionally substituted acyl groups; and

$R^{12}$ and $R^{13}$ are independently selected from the group consisting of H, optionally substituted alkyl groups, optionally substituted alkenyl groups, optionally substituted alkynyl groups, optionally substituted aryl groups, and optionally substituted acyl groups and pharmaceutically acceptable salts thereof.

Compounds of formulae I and II are also potentially useful in the treatment and prevention of mammalian disease states characterized by abnormal calcium regulation, cell proliferation, immune response, dermatological conditions, and/or neurodegenerative conditions.

Examples of disease states characterized by abnormal calcium regulation include osteoporosis, humoral hypercalcemia of malignancy, renal osteodystrophy, and certain types of renal failure. Examples of disease states characterized by abnormal cell proliferation include leukemia, cancers, and psoriasis. Examples of disease states characterized by abnormal immune response include psoriasis, host-graft rejection, lupus, multiple sclerosis, autoimmune induced diabetes, scleroderma, and rheumatoid arthritis. Examples of disease states characterized by abnormal dermatological conditions include acne, alopecia, wrinkles, insufficient sebum secretion, insufficient dermal hydration, and insufficient dermal firmness. An example of a neurodegenerative condition is Alzheimer's disease.

In addition to the VDR modulating activities of the compounds of formula I, the inventors have also discovered heretofore unknown non-secosteroidal compounds of formula II:

wherein:

X and Y are each independently selected from the group consisting of O, S, and $NR^7$;

Z is selected from the group consisting of C=O, $CH(OR^8)$, and $CH(NR^9R^{10})$;

$R^1$ and $R^2$ are independently selected from the group consisting of alkyl groups, optionally fluorinated; or together $R^1$ and $R^2$ form a cycloalkylidene having 3 to 8 carbon atoms, optionally fluorinated;

$R^3$ and $R^4$ are independently selected from the group consisting of halogen; lower n-alkyl, optionally fluorinated; and lower alkoxy, optionally fluorinated;

$R^5$ is selected from the group consisting of H; optionally substituted alkyl groups; optionally substituted alkenyl groups; optionally substituted alkynyl groups; optionally substituted aryl groups; $OR^{11}$; $NR^{12}R^{13}$; or together with $R^8$, $R^9$, or $R^{10}$ forms a 3- to 12-membered cyclic group wherein said cyclic group is selected from the group consisting of amidines, amines, ethers, lactams, lactones, ketals, hemiketals, aminals, hemiaminals, carbonates, carbamates, ureas, and combinations thereof;

$R^6$ is selected from the group consisting of H and alkyl groups, optionally substituted;

$R^7$ is selected from the group consisting of H and alkyl groups, optionally substituted;

$R^8$ is selected from the group consisting of H, optionally substituted alkyl groups, optionally substituted alkenyl groups, optionally substituted alkynyl groups, optionally substituted aryl group, and optionally substituted acyl groups;

$R^9$ and $R^{10}$ are independently selected from the group consisting of H, optionally substituted alkyl groups, optionally substituted alkenyl groups, optionally substituted alkynyl groups, optionally substituted aryl groups, and optionally substituted acyl groups;

$R^{11}$ is selected from the group consisting of H, optionally substituted alkyl groups, optionally substituted alkenyl groups, optionally substituted alkynyl groups, optionally substituted aryl groups, and optionally substituted acyl groups; and $R^{12}$ and $R^{13}$ are independently selected from the group consisting of H, optionally substituted alkyl groups, optionally substituted alkenyl groups, optionally substituted alkynyl groups, optionally substituted aryl groups, and optionally substituted acyl groups and pharmaceutically acceptable salts thereof; with the provisos that:

a. when X and Y are both O, Z is C=O, and $R^5$ is selected from the group consisting of OH and $C_1$–$C_4$ alkoxy, then $R^6$ is not carboxymethyl and alkyl esters thereof;

b. when X and Y are both O, and Z is selected from the group consisting of $CH(OR^8)$ and $CH(NR^9R^{10})$, then $R^5$ is not H or primary alkyl;

C. when X and Y are both O, and Z is $CH(OR^8)$, then $R^6$ and $R^8$ do not both comprise aziridines;

d. when X and Y are both O, and Z is $CH(OR^8)$, then $R^5$, $R^6$, and $R^8$ do not simultaneously comprise alkenyl ethers; and e. when X and Y are both O, and Z is $CH(OR^8)$, then $R^5$ and $R^6$ do not both comprise glycidyl ethers.

1. Preferred Compounds

In preferred compounds of formulae I and II, suitable alkyl groups include those of from 1 to about 20 carbon atoms. Suitable alkenyl groups include those from 2 to about 20 carbon atoms. Suitable alkynyl groups include those from 2 to about 20 carbon atoms. Suitable acyl groups include those from 1 to about 20 carbon atoms. Suitable aryl groups include those from 5 to about 20 total carbon and heteroatoms.

Preferred $R^1$ and $R^2$ groups include ethyl or, where $R^1$ and $R^2$ together form a cyloalkylidene, includes cyclohexylidene.

Preferred $R^3$ and $R^4$ groups include methyl and chloro. A particularly preferred $R^3$ and $R^4$ group is methyl.

Preferred $R^5$ groups include alkyl and hydroxy. A particularly preferred $R^5$ group is t-butyl.

Preferred $R^6$ groups include oxygen substituted alkyl, for example:

Particularly preferred $R^6$ groups are 2,3-epoxypropyl, 2-oxo-3,3-dimethylbutyl and 2-hydroxy-3,3-dimethylbutyl.

Preferred X and Y groups include O.

Preferred Z groups include C=O and $CH(OR^8)$. Particularly preferred Z groups are C=O and CH(OH).

Most preferred compounds include:

1,1-bis[3-methyl-4-(3,3-dimethyl-2-oxobutoxy)phenyl] cyclohexane (compound 4, Example 2);

3,3-bis[3-methyl-4-(3,3-dimethyl-2-oxobutoxy)phenyl] pentane (compound 7, Example 4);

3-[3-methyl-4-(2,3-epoxypropoxy)phenyl]-3-[3-methyl-4-(3,3-dimethyl-2-oxobutoxy)phenyl]pentane (compound 9, Example 6);

3-[3-methyl-4-(2-hydroxy-3,3-dimethylbutoxy)phenyl]-3-[3-methyl-4-(3,3-dimethyl-2-oxobutoxy)phenyl]pentane (compound 11, Example 8);

3-[3-methyl-4-(2,3-dihydroxypropoxy)phenyl]-3-[3-methyl-4-(2-hydroxy-3,3-dimethylbutoxy)phenyl]pentane (compound 13, Example 10).

It will be apparent to one skilled in the art that many of the compounds of formulae I and II exist as stereoisomers, that is E/Z isomers, enantiomers and/or diastereomers; the present invention includes both the stereoisomerically pure compounds of formulae I and II as well as any stereoisomeric mixtures thereof. The scope of the present invention encompasses tautomers of compounds of formulae I and II, where appropriate. The present invention is also embodied in mixtures of compounds of formulae I and II. The skilled artisan will also appreciate that the family of compounds of formulae I and II include acidic and basic members and that the present invention includes pharmaceutically acceptable salts thereof.

2. Preparation of Preferred Compounds

Figure 2:
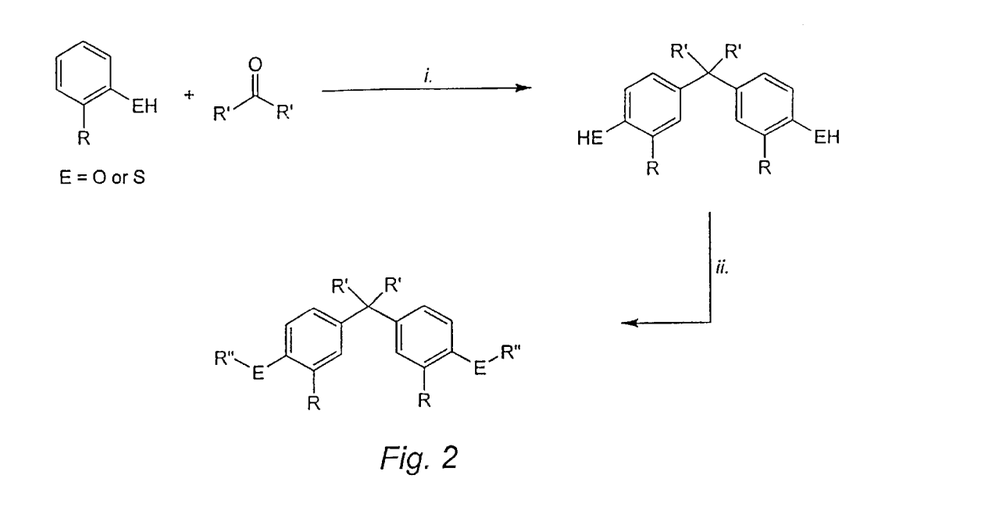
FIG. 2 is a general scheme for the synthesis of ether and thioether compounds of formulae I and II. In this figure, (i) and (ii) are defined as follows: (i) acid-catalyzed aromatic substitution; (ii) alkylation.
Figure 3:
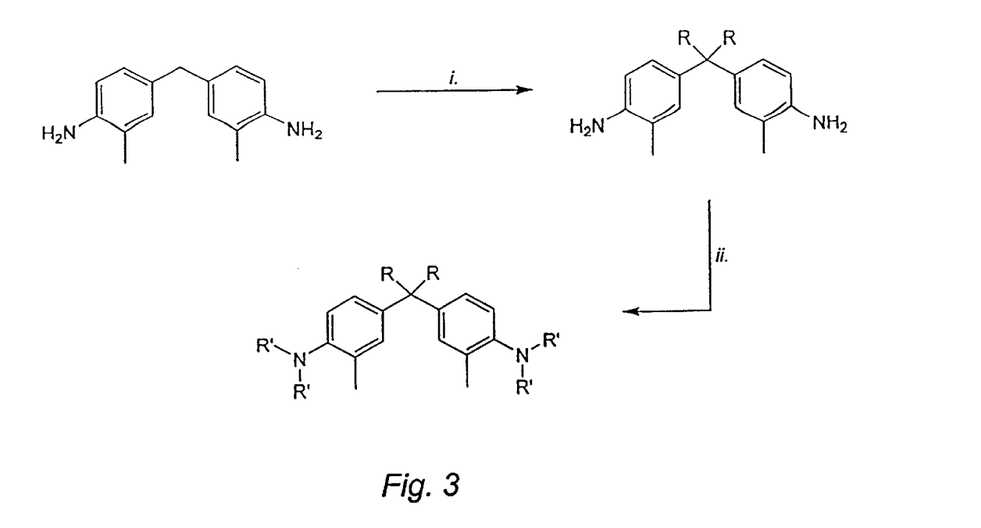
FIG. 3 is a general scheme for the synthesis of amine compounds of formula I and II. In this figure, (i) and (ii) are defined as follows: (i) oxidation and quaternization of the doubly-benzylic position; (ii) alkylation.

Compounds of formulae I and II may be conveniently synthesized as shown in FIGS. 2 and 3. In FIG. 2, two 2-substituted phenols or thiophenols sequentially undergo electrophilic, aromatic substitution to provide diphenols or dithiophenols. A vast array of 2-substituted phenols and thiophenols are known and their synthetic methods well established (Phenols: *Houben-Weyl Methoden der organischen Chemie*, V6, part 1c. Thiophenols: *Houben-Weyl Methoden der organischen Chemie*, V9, E11.); many are available commercially (from, for example, the Aldrich Chemical Company). The first electrophile derives from protonation of ketone; the second is the carbenium ion derived from protonation of the tertiary-alcohol product of the first reaction.

These diphenols or dithiophenols may then be alkylated to ethers or thioethers in a single step to afford symmetrically disposed compounds, or in two steps to provide unsymmetrical compounds. Such alkylation reactions are well known in the art and may be conveniently accomplished, for example, with sodium hydride followed by an alkyl halide, or by epoxide or aziridine openings. These appendages may be further modified as desired using methodologies well known in the art.

FIG. 3 shows the preparation of the amine members of formulae I and II. The commercially available 4,4'-methylenedianiline (Aldrich Chemical Company) is elaborated by oxidation at the doubly benzylic position, followed by conversion to a quaternary center using any number of methods known in the art. For example, the dianiline may be oxidized with selenium dioxide to the benzylic alcohol which may be oxidized to the ketone. This ketone may be converted to a quaternary carbon in a single step, for example, with the Reetz titanium reagent, or alternatively, in several steps, for example by aldol condensation followed by conjugate addition, or by other methods well known in the art.

Alkylations of nitrogen atoms are also well known in the art. Such alkylations are readily accomplished with alkyl halides, for example. Another well known alkylation method is reductive alkylation using an aldehyde or ketone and a reducing agent, for example, sodium cyanoborohydride. Still another method is acylation followed by reduction. The skilled artisan is filly aware that the alkylation and quaternization steps may be transposed or even interposed depending on the particular compound of interest.

The specific syntheses of compounds 4, 7, 9, 11, and 13 are described in detail in the Examples.

3. Selection of Preferred Compounds

The present invention relates to non-secosteroidal compounds with vitamin $D_3$ activity. The active form of vitamin $D_3$, 1,25-dihydroxyvitamin $D_3$ [1,25(OH)$_2D_3$], shows both inimunosuppressive and antiproliferative effects in vitro and in vivo and has been used to treat kidney failure and psoriasis in humans. The only known side-effect of 1,25 (OH)$_2D_3$ is the mobilization of calcium; higher doses, can lead to hypercalcemia, a potentially life-threatening condition.

Non-secosteroidal VDR activators may display different profiles of activity than 1,25(OH)$_2D_3$ and secosteroidal analogs thereof, including reduced calcemic effects which would render them attractive as both oral and topical pharmaceuticals and chemopreventatives for a number of disease states. The inventors have compared the activities of compounds of the present invention with 1,25(OH)$_2D_3$ in the inhibition of cancer cell growth and keratinocyte growth in vitro, differentiation of leukemic cells in culture, and in vivo regulation of a vitamin D target gene and serum calcium levels. These experiments are detailed in Example A and summarized in Tables 1 and 2.

Additionally, these vitamin D mimics do not bind serum DBP in vitro. The ability of various 1,25(OH)$_2D_3$ analogs to bind serum vitamin D binding protein (DBP) has been associated with their ability to raise serum calcium in vivo: analogs with lowered affinity for DBP showed lowered calcium potential in animal models (A. S. Dusso et al. *Endocrinology* 1991, 128, 1687–1692). In the DBP-binding assays, none of the vitamin D mimics tested bound appreciably to either rat or human DBP, showing IC$_{50}$ values greater than 10 $\mu$M. These results imply that this series of vitamin D mimics may be less calcemic in vivo than 1,25(OH)$_2D_3$. These experiments are also detailed in Example A and summarized in Table 1 in the Examples.

In vivo experiments in mice of the effects of compound 4 and 1,25(OH)$_2D_3$ on kidney 24(OH)ase RNA levels and serum calcium levels are described in Example B and the results summarized in Table 2 in the Examples. The higher ratio of target gene induction vs calcium concentration indicates a greater separation of these effects for 4 than for 1,25(OH)$_2D_3$.

Figure 1A:
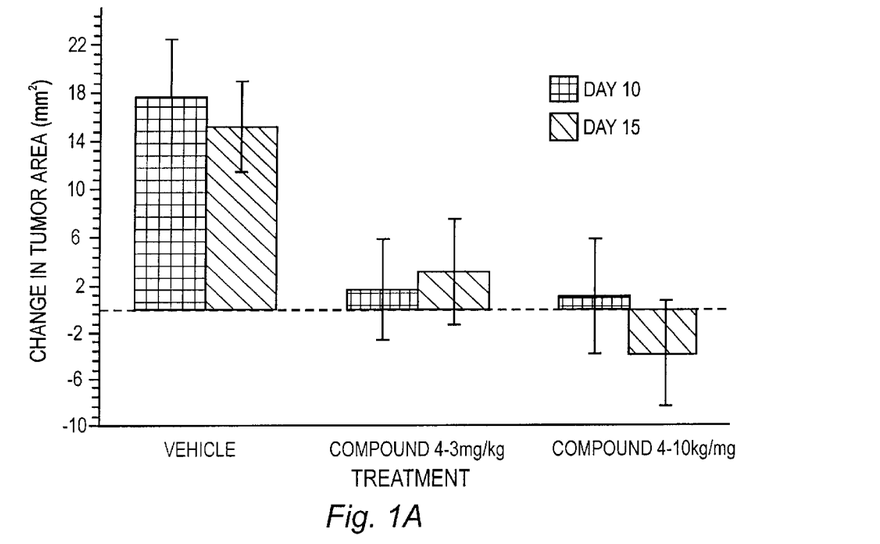
FIGS. 1A and 1B depict the In vivo efficacy of compound 4 in LNCaP tumor growth inhibition in nude mice without hypercalcemia.
Figure 1B:
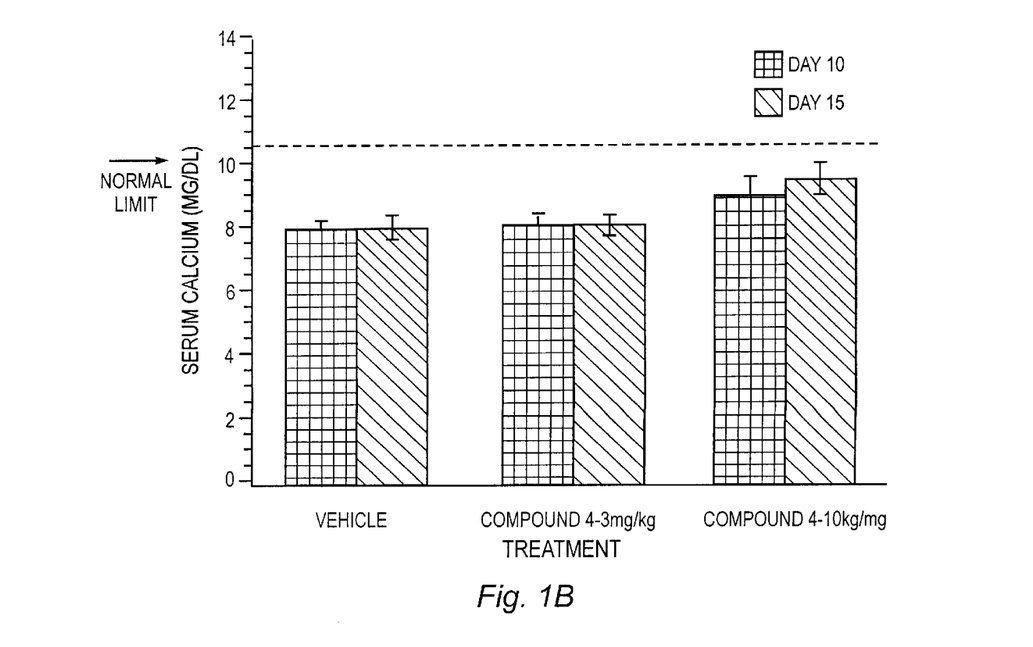

One of the compounds (4) that showed a good separation of target gene regulation from serum calcium elevation was tested in a nude mouse prostate cancer model, the results of which are summarized in FIG. 1. In Example C, the effect of compound 4 on nude mice injected subcutaneously with LNCaP prostate cancer cells was studied. FIG. 1 displays results of compound 4 vs vehicle in these experiments. As shown in FIG. 1*a*, mice treated with compound 4 showed decreased tumor growth rates as compared to the control group. FIG. 1*b* shows that hypercalcemia was not observed at these dosage levels of compound 4.

The vitamin D3 or vitamin D mimics of the invention may be used alone or in combination with other drugs or treatments. In particular, the compounds of the invention can be used in combination with retinoids, particularly RXR selective retinoids ("rexinoids"; see, e.g. U.S. Pat. No. 5,780,676 and published international application WO 97/12853) or androgen receptor modulators (see, e.g. U.S. Pat. Nos. 5,677,336, 5,696,133, 5,696,130, and 5,693,646) to treat cancer, particularly prostate cancer.

4. Pharmaceutical Compositions

In another aspect, the present invention encompasses pharmaceutical compositions prepared for storage or administration which comprise a therapeutically effective amount of one or more compounds of the present invention in a pharmaceutically acceptable carrier.

The therapeutically effective amount of a compound of the present invention will be in the range of about 1 $\mu$g/kg to about 50 mg/kg. The particular dosage will depend on the route of administration, the type of mammal being treated, and the physical characteristics of the specific mammal under consideration, as well as the characteristics of the specific compound: for example, potency, bioavailability, metabolic characteristics, etc. These factors and their relationship to determining this amount are well known to skilled practitioners in the medical arts. This amount and the mode of administration can be tailored to achieve optimal efficiency and will be contingent on myriad factors recognized by those skilled in the medical arts, including weight, diet, and concurrent medication. The therapeutically effective amount of the compounds of the present invention can range broadly depending upon the desired effects and the therapeutic indication.

Pharmaceutically acceptable carriers for therapeutic use are well known in the pharmaceutical art, and are described, for example, in *Remington's Pharmaceutical Sciences*(A. P. Gennaro, ed.; Mack, 1985). For example, sterile saline or phosphate-buffered saline at physiological pH may be used. Preservatives, stabilizers, dyes, and even flavoring agents may be provided in the pharmaceutical composition. For example, sodium benzoate, sorbic acid, and esters of p-hydroxybenzoic acid may be added as preservatives (Id at 1449). Antioxidants and suspending agents may also be used (Id).

The pharmaceutical compositions of the present invention may be formulated and used as tablets, capsules, or elixirs for oral administration; suppositories for rectal or vaginal administration; sterile solutions and suspensions for parenteral administration; creams, lotions, or gels for topical administration; aerosols or insufflations for intratracheobronchial administration; and the like. Preparations of such formulations are well known to those skilled in the pharmaceutical arts. The dosage and method of administration can be tailored to achieve optimal efficacy and will depend on factors which those skilled in the medical arts will recognize.

When administration is to be parenteral, such as intravenous on a daily basis, injectable pharmaceuticals may be prepared in conventional forms, either as liquid solutions or suspensions; solid forms suitable for solution or suspension in liquid prior to injection; or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g. liposomes) may be utilized.

The compounds of this invention and their preparation can be understood further by the examples which illustrate some of the processes by which these compounds are prepared. The examples should not, however, be construed as specifically limiting the invention and variations of the invention, now known or later developed, are considered to fall within the scope of the present invention as hereinafter claimed.

EXAMPLES

Example 1
Preparation of 1,1-bis[4-hydroxy-3-methylphenyl] cyclohexane (3).

To a solution of o-cresol (5 g, 46.3 mmol) and cyclohexanone (2 g, 20.4 mmol) in acetic acid (20 mL) was added conc $H_2SO_4$ (4 mL). The reaction mixture was stirred at ambient temperature for 3 days, poured over ice, and diluted with 1:5 ethyl acetate/hexanes. The organic fraction was separated, washed with water and brine, dried over $MgSO_4$, and concentrated in vacuo. Chromatography (silica, 5% ethyl acetate in hexanes) afforded 1.8 g of diphenol 3. $^1$HNMR ($CDCl_3$) δ: 6.98 (d, J=2 Hz, 2 H, Ar—H), 6.95 (dd, J=2 Hz, J=8.6 Hz, 2 H, Ar—H), 6.64 (d, J=8.6 Hz, 2 H, Ar—H), 2.19 (s, 6 H, Ar—$CH_3$), 2.19 (m, 4 H, $CH_2$), 1.27–1.52 (m, 6 H, $CH_2$).

Example 2
Preparation of 1,1-bis[3-methyl-4-(3,3-dimethyl-2-oxobutoxy)phenyl]cyclohexane (4).

To a solution of the compound of Example 1 (1.0 g, 3.37 mmol) in DMF (10 mL) was added NaH (306 mg, 8.00 mmol). The reaction mixture was stirred 5 min and chloropinacolone (1.07 g, 8.00 mmol) was added. The reaction mixture was stirred 30 min, then quenched with water and diluted with ethyl acetate. The organic fraction was separated, washed with water and brine, dried over $MgSO_4$, and concentrated in vacuo. Chromatography (silica, 10% ethyl acetate in hexanes) afforded 820 mg (1.66 mmol) of 4. $^1$HNMR ($CDCl_3$) δ: 7.09 (d, J=2 Hz, 2 H, Ar—H), 6.96 (dd, J=2 Hz, J=8.6 Hz, 2 H, Ar—H), 6.51 (d, J=8.6 Hz, 2 H, Ar—H), 4.82 (s, 4 H, $CH_2O$), 2.25 (s, 6 H, Ar—$CH_3$), 2.19 (m, 4 H, $CH_2$), 1.27–1.52 (m, 6 H, $CH_2$), 1.25 (s, 18 H, t-Bu).

Example 3
Preparation of 3,3-bis[4-hydroxy-3-methyl]pentane (6).

To a solution of o-cresol (5 g, 46.3 mmol) and 3-pentanone (2 g, 23.2 mmol) in acetic acid (20 mL) was added conc $H_2SO_4$ (4 mL). The reaction mixture was stirred at ambient temperature for 3 days, poured over ice, and diluted with 1:5 ethyl acetate/hexanes. The organic fraction was separated, washed with water and brine, dried over $MgSO_4$, and concentrated in vacuo. Chromatography (silica, 5% ethyl acetate in hexanes) afforded 2.2 g of diphenol 6. $^1$HNMR ($CDCl_3$) δ: 6.90 (d, J=2 Hz, 2 H, Ar—H), 6.95 (dd, J=2 Hz, J=8.6 Hz, 2 H, Ar—H), 6.64 (d, J=8.6 Hz, 2 H, Ar—H), 2.21 (s, 6 H, Ar—$CH_3$), 2.0 (q, J=7.3 Hz, 4 H, $CH_2CH_3$), 0.60 (t, J=7.3 Hz, 4 H, $CH_2CH_3$).

Example 4
Preparation of 3,3-bis[3-methyl-4-(3,3-dimethyl-2-oxobutoxy)phenyl]pentane (7).

Compound 7 was prepared analogously to Compound 4 except that the compound of Example 3 (6) was used instead of the compound of Example 1 (3). $^1$HNMR ($CDCl_3$) δ: 6.89 (m, 4 H, Ar—H), 6.49 (d, J=8.3 Hz, 2 H, Ar—H), 4.82 (s, 4 H, $CH_2O$), 2.23 (s, 6 H, Ar—$CH_3$), 2.00 (q, J=7.3 Hz, 4 H, $CH_2CH_3$), 1.23 (s, 18 H, t-Bu), 0.58 (t, J=7.3 Hz, 6 H, $CH_2CH_3$).

Example 5
Preparation of 3-[4-hydroxy-3-methylphenyl]-3-[3-methyl-4-(2,3-epoxypropoxy)phenyl]pentane (8).

To a solution of the compound of Example 3 (1.0 g, 3.5 mmol) in DMF (10 mL) was added NaH (8.4 mg, 3.5 mmol).

The reaction mixture was stirred for 5 min, then chloropinacolone (471 mg, 3.5 mmol) was added. The reaction mixture was stirred 30 min, then quenched with water and diluted with ethyl acetate. The organic fraction was separated, washed with water and brine, dried over MgSO₄, and concentrated in vacuo. Three compounds were observed by TLC, the desired product corresponding to the middle compound. Chromatography (silica, 10% ethyl acetate in hexanes) afforded 250 mg (0.57 mmol, 16%) of 8.

Example 6
Preparation of 3-[3-methyl-4-(2,3-epoxypropoxy)phenyl]-3-[3-methyl-4-(3,3-dimethyl-2-oxobutoxy)phenyl]pentane (9).

To a solution of the compound of Example 5 (80 mg, 0.21 mmol) in anhydrous DMF (1 mL) was added NaH (5.5 mg, 0.23 mmol). The reaction mixture was stirred 30 min at ambient temperature, then epichlorohydrin (22.0 mg, 0.23 mmol) was added. The reaction was heated to 120° C. for 1 hr or until the reaction was complete by TLC (20% ethyl acetate in hexanes). The reaction mixture was cooled, quenched with water, and diluted with ethyl acetate. The organic fraction was separated, washed with water and brine, dried over MgSO₄, and concentrated in vacuo. Chromatography (silica, 10% ethyl acetate in hexanes) afforded 30 mg (0.07 mmol, 33%) of 9. $^1$HNMR (CDCl₃) δ: 6.89 (m, 4 H, Ar—H), 6.66 (d, J=8.3 Hz, 1 H, Ar—H), 6.49 (d, J=8.3 Hz, 1 H, Ar—H), 4.83 (s, 2 H, CH₂), 4.18 (dd, J=11.3 Hz, J=3.3 Hz, 1 H, CH₂), 3.95 (dd, J=11.3 Hz, J=3.3 Hz, 1 H, CH₂), 3.35 (m, 1 H, CH), 2.90–2.76 (m, 2 H, CH₂), 2.23 (s, 3 H, Ar—CH₃), 2.18 (s, 3 H, Ar—CH₃), 2.00 (q, J=7.3 Hz, 4 H, CH₂CH₃), 1.24 (s, 18 H, t-Bu), 0.59 (t, J=7.3 Hz, 6 H, CH₂CH₃).

Example 7
Preparation of 3-[4-hydroxy-3-methylphenyl)-3-[3-methyl-4-(2-hydroxy-3,3-dimethylbutoxy)phenyl]pentane (10).

The compound of Example 5 (240 mg, 0.63 mmol) was dissolved in methanol (2.5 mL) and the solution cooled to 0° C. To this solution was added NaBH₄ (24.0 mg, 0.63 mmol) and the reaction stirred 20 min. The reaction was quenched with saturated, aqueous NH₄Cl and extracted with ethyl acetate. The organic fraction was separated, washed with water and brine, dried over MgSO₄, and concentrated in vacuo. Chromatography (silica) afforded 160 mg (0.42 mmol) of 10.

Example 8
Preparation of 3-[3-methyl-4(2-hydroxy-3,3-dimethylbutoxy)phenyl]-3-[3-methyl-4-(3,3-dimethyl-2-oxobutoxy)phenyl]pentane (11).

To a solution of the compound of example 7 (100 mg, 0.26 mmol) in DMF (2.5 mL) was added NaH (7.0 mg, 0.29 mmol). The reaction mixture was stirred at ambient temperature for 30 min, then pinacolone (39 mg, 0.29 mmol) was added. The reaction was stirred at ambient temperature for 1 h or until judged complete by TLC (20% ethyl acetate in hexanes). The reaction mixture was quenched with water, and diluted with ethyl acetate. The organic fraction was separated, washed with water and brine, dried over MgSO₄, and concentrated in vacuo. Chromatography (silica, 10% ethyl acetate in hexanes) afforded 117 mg (0.24 mmol, 92%) of 11. $^1$HNMR (CDCl₃) δ: 6.91 (m, 4 H, Ar—H), 6.69 (d, J=8.3 Hz, 1 H, Ar—H), 6.49 (d, J=8.3 Hz, 1 H, Ar—H), 4.83 (s, 2 H, CH₂), 4.09 (dd, J=11.3 Hz, J=3.3 Hz, 1 H, CH₂), 3.85 (t, J=11.3 Hz, 1 H, CH₂), 3.69 (d, J=11.3 Hz, 1 H, CH₂), 2.23 (s, 3 H), Ar—CH₃), 2.18 (s, 3 H, Ar—CH₃), 2.00 (q, J=7.3 Hz, 4 H, CH₂CH₃), 1.24 (s, 9 H, t-Bu), 1.00 (s, 9 H, t-Bu), 0.58 (t, J=7.3 Hz, 6 H, CH₂CH₃).

Example 9
Preparation of 3-[3-methyl-4-(2,3-dihydroxypropoxy)phenyl]-3-[3-methyl-4-(3,3-dimethyl-2-hydroxybutoxy)phenyl]pentane (12).

To a solution of the compound of Example 5 (200 mg, 0.52 mmol) in anhydrous DMF (4 mL) was added NaH (14.0 mg, 0.58 mmol). The reaction was stirred 20 min, then glycidol (43.0 mg, 0.58 mmol) was added. The reaction mixture was warmed to 80° C. for 1 hr and cooled. The reaction mixture was quenched with water, and diluted with ethyl acetate. The organic fraction was separated, washed with water and brine, dried over MgSO₄, and concentrated in vacuo. Chromatography (silica, 10% ethyl acetate in hexanes) afforded 117 mg (0.26 mmol, 50%) of 12.

Example 10
Preparation of 3-[3-methyl-4-(2,3-dihydroxypropoxy)phenyl]-3-[3-methyl-4-(2-hydroxy-3,3-dimethylbutoxy)phenyl]pentane (13).

The compound of Example 9 (70 mg, 0.15 mmol) was dissolved in methanol (2.5 mL) and the solution cooled to 0° C. To this solution was added NaBH$_4$ (5.7 mg, 0.15 mmol) and the reaction stirred 20 min. The reaction was quenched with saturated, aqueous NH$_4$Cl and extracted with ethyl acetate. The organic fraction was separated, washed with water and brine, dried over MgSO$_4$, and concentrated in vacuo. Chromatography (silica) afforded 23 mg (0.05 mmol, 33%) of 13. $^1$HNMR (CDCl$_3$) δ: 6.94 (m, 4 H, Ar—H), 6.69 (d, J=8.3 Hz, 2 H, Ar—H), 4.12–4.02 (m, 4 H), 3.88–3.67 (m, 4 H), 2.17 (s, 3 H, Ar—CH$_3$), 2.16 (s, 3 H, Ar—CH$_3$), 2.04 (q, J=7.3 Hz, 4 H, CH$_2$CH$_3$), 1.00 (s, 9 H, t-Bu), 0.59 (t, J=7.3 Hz, 6 H, CH$_2$CH$_3$).

Example A
In vitro and Cell-Based Assays.

Cotransactivation properties. Hep G2 (human hepatoma, ATCC) cells were cotransfected with plasmid encoding human VDR (A.R. Baker et al. *Proc. Natl. Acad. Sci.* 1988, 85, 3294–3298; A. Zou et al. *J. Biol. Chem.* 1997, 272, 19027–19034) driven by a strong constitutive promoter (RSV) and a reporter plasmid encoding luciferase driven by the natural VDRE located within the h24(OH)ase promoter (Zou et al. 1997). Reporter and receptor containing vectors were transfected along with carrier DNA and β-galactosidase internal control plasmid as previously described except that Hep G2 cells were used (Id). Briefly, transfections were performed in triplicate in 96-well gelatin-coated plates with a total of 20 μg/mL DNA (0.5 μg receptor expression vector, 5 μg reported plasmid, 5 μg β-galactosidase plasmid, and pGEM carrier DNA to 20 μg) of calcium phosphate-HEPES transfection solution. Six hours later, 1,25(OH)$_2$D$_3$ or compounds of formula I ($10^{-12}$–$10^{-5}$ M) were added and the cells incubated 40 h. Cells were lysed, and luciferase and β-galactosidase activities measured as previously described (Id). Luciferase values were normalized with β-galactosidase values to control for variable transfection efficiencies. No reporter-driven luciferase activity was observed without VDR cotransfection, indicating the VDR-dependency of the compounds. Ligand concentration yielding 50% induction of luciferase activity EC$_{50}$) of 1,25(OH)$_2$D$_3$ was ~2–10 nM for 1,25(OH)$_2$D$_3$, whereas EC$_{50}$ for the compounds of the invention range from 3 μM–20 nM.

VDR binding. Human VDR (Baker et al. 1988) was constructed into a yeast expression plasmid as described previously (D. P. McDonnell et al. *Mol Cell Biol.* 1989, 9, 3517–3523). Cell extracts from yeast transformants were prepared and full length VDR expression was confirmed by Western blotting. Crude yeast cell protein extracts containing hVDR (4 μg/tube) were used for saturation and Scatchard analyses using tritiated 1,25(OH)$_2$D$_3$ (Amersham). Hydroxylapatite resin was used to separate bound from unbound ligand as described previously (E. A. Allegretto et al. *J. Biol. Chem.* 1993, 268, 26625–26633). The resultant K$_d$ value of ~0.5 nM is in agreement with published values for 1,25(OH)$_2$D$_3$ binding to VDR. Competition analyses were performed at 2 nM of tritiated 1,25(OH)$_2$D$_3$ and 0.1 nM–10 μM of the invented compounds. Binding buffer contained 10 mM Tris,pH 7.5, 1 mM DTT, and 0.4 M KCl; wash buffer contained 10 mM Tris, 100 mM KCl, and 10 mM CHAPS detergent.

Cancer cell growth inhibition and analysis. SK-BR-3 human breast cancer cells (ATCC) and LNCaP human prostate cancer cells (ATCC) were plated in 96-well, flat-bottomed microtiter plates (CoStar) with 50 μL serum-containing media/well. All cell growth assays were carried-out in media containing 5–7.5% FBS. Cell plating numbers (cells/well) were as follows: SK-BR-3, 3000 (3-day assays); LNCAP, 1000 (4-day assays). Cell plating number was determined by growth rate of each cell line and duration of the assay. Cells treated with vehicle were~80% confluent by the end of each assay. Cells were allowed to adhere for 24 h prior to compound addition as follows:

Ten-fold serial dilutions were performed with changing of pipette tips between each dilution. Diluted compounds were then added to the cells (50 μL/well) to final concentrations of $1\times10^{-5}$–$1\times10^{-11}$ M (1% ethanol) in triplicate. Cells and ligands were incubated at 37° C. for 3–4 days. BrdU (5-bromo-2'-deoxyuridine) incorporation was analyzed as a measure of DNA replication (Cell Proliferation ELISA kit, Boehringer) and absorbance was measured at 450 nm.

One row of wells contained media only and these absorbance values were averaged as background and then subtracted from absorbance values from each individual well containing cells. The average values were then determined for each triplicate and plotted vs ligand concentration. The average vehicle (1% ethanol) value was determined, less the background average. This value is displayed on graphs as a single point at 0 M and is denoted as a solid diamond. Efficacy (% growth inhibition) was determined as [1–(O.D. at maximal response with compound/O.D. of average vehicle)]×100. Potency (EC$_{50}$) was determined as the concentration of compound that elicited half-maximal response.

Leukemic cell differentiation. HL60 human promyelocytic leukemia cells (ATCC) were grown in media containing 15% FBS and plated at 100,000 cells/mL in 10 cm dishes or in 6 well plates. Ligands were added in ethanol vehicle (1%) at various concentrations for 5 days without changing the media. On the fifth day, cells were harvested and assayed for markers of differentiation. The ability of the cells to reduce the dye nitroblue tetrazolium (NBT) is the standard method for determination of differentiation of these cells (S. J. Collins et al. *J. Exp. Med.* 1979, 149, 969–974). Cells that bioreduce the dye turn blue-black and represent differentiated cells, and are counted. Undifferentiated cells are clear and are also counted; percent differentiated cells are then determined from the two numbers. To determine that the cells were differentiated into macrophages/monocytes (vitamin D-induced pathway), the cell surface protein marker, CD14, was assayed by FACS analysis (F. Oberg et al. *J Immunol.* 1993, 150, 3487–3495). EC$_{50}$ values represent the concentration of ligand that induced 50% of the cells to be NBT formazan-positive or CD14-positive.

Keratinocyte growth inhibition. Normal human epidermal keratinocytes (NHEK) were grown according to vendor specifications (Clonetics, San Diego). BrdU assays were performed as above except that cells were plated at 200 cells per well (96-well plates) and fresh media with ligands were added on day 0 and day 2; BrdU assays were run on day 4.

Serum DBP-binding. DPB competition binding assays were performed by a literature method (Dusso et al. 1991). The source of DBP was either human serum (Scantibodies) or rat serum (Gibco-BRL) diluted 1:10,000 in sodium phosphate buffer (pH 7.4). Sera were incubated for 2 h at 4° C. with 2 nM [$^3$H]-25(OH)D$_3$ (Amersham) with and withoun unlabeled 25(OH)D$_3$ or 1,25(OH)2D3 (0.01 nM–1 μM), or unlabeled vitamin D mimic compounds (10 nM–10 μM). Bound ligand was separated from unbound ligand with Dextran-coated charcoal in gelatin-phosphate buffer.

Table 1 summarizes the experimental results for compounds 4, 7, 9, 11, and 13 in in vitro VDR binding and serum vitamin D binding protein (DBP) assays and various cell-based assays: Hep G2 cell cotransactivation, leukemic cell differentiation, prostate and breast cancer cell growth inhibition, and growth inhibition of primary keratinocytes.

nocyte growth and elicited monocytic differentiation of HL60 leukemia cells in vitro.

Example B

In vivo gene regulation and calcium potential. Balb/c mice (male 6–8 weeks old, ~20 g) were fed a vitamin D deficient, calcium replete diet (Purina Mills) for 7–14 days prior to receiving treatment with compounds. Animals were housed under normal lighting. Compounds were administered in sesame oil vehicle with 4% ethanol by oral gavage (0.1 mL dose volume). Dosing was daily for 3–5 days (3–4 animals/dosing group). On the final day of dosing, 4–6 h after the final dose, animals were euthanized, the kidneys removed and blood collected. Serum was prepared from the blood and calcium determination performed by colorimetric assay (Sigma). Kidneys were homogenized in guanidine

TABLE 1

Activity of compounds 4, 7, 9, 11, and 13 in in vitro and cell-based assays.

| Compound | VDR binding[a] | DBP binding[b] | CTF[c] | HL60[d] | LNCaP[e] | SK-BR-3[f] | NHEK[g] |
|---|---|---|---|---|---|---|---|
| 4 | >10,000 | >10,000 | 2200 | 2000 | 2000 | 2000 | 500 |
| 7 | >10,000 | >10,000 | 600 | 800 | 300 | 800 | 500 |
| 9 | >10,000 | >10,000 | 60 | 150 | 100 | 150 | 200 |
| 11 | >10,000 | >10,000 | 400 | 400 | 500 | 500 | ND[h] |
| 13 | 150 | >10,000 | 40 | 30–50 | 20 | 30–50 | 30–50 |
| 1,25(OH)$_2$D$_3$ | 0.5 | 200 (h) 40 (r) | 2–5 | 8–10 | 2 | 8–10 | 10–30 |

[a]$K_i$ values (nM) determined by in vitro competitive binding to hVDR vs [$^3$H]-1,25(OH)$_2$D$_3$.
[b]$IC_{50}$ values (nM) from binding in vitro to rat (r) or human (h) serum DBP by competition with [$^3$H]-25(OH)D$_3$.
[c]$EC_{50}$ values (nM) determined by cotransactivation assays with cotransfected VDRE-luciferase reporter (Zou, et al. 1997) and human VDR in Hep G2 cells.
[d]$EC_{50}$ values (nM) determined by nitroblue tetrazolium and CD14 assays of differentiation of HL60 premyelocytic cells into macrophages/monocytes.
[e]$EC_{50}$ values (nM) determined by growth inhibition of LNCaP prostate cancer cells by BrdU incorporation.
[f]$EC_{50}$ values (nM) determined by growth inhibition of SK-BR-3 breast cancer cells by BrdU incorporation.
[g]$EC_{50}$ values (nM) determined by growth inhibition of human epidermal keratinocytes by BrdU incorporation.
[h]Not determined.

These results show that the vitamin D mimics elicit VDR dependent transcription in a cotransfection assay. These results also show that the non-secosteroidal vitamin D mimics of the invention do not bind to serum DBP which indicates that the compounds may have a reduced potential to cause undesirable calcium mobilization effects. These results also show that the non-secosteroidal vitamin D mimics of the invention inhibited cancer cell and keraticontaining buffer and RNA prepared as described previously (E. A. Allegretto et al. *J. BioL Chem.* 1995, 270, 23906–23909). 15–20 μg total RNA was utilized in Northern blot analysis using rat 24(OH)ase probe; GAPDH probe was used to normalize for RNA loading, as described previously (Id). Quantitation was by PhosphorImager analysis. Results are summarized in Table 2.

TABLE 2

Analysis of vitamin D target gene induction and serum calcium levels in mice treated with 1,25(OH)$_2$D$_3$, 4, or 7.

| Compound | Dose | Relative 24(OH)ase activity[a] | Serum Ca$^{2+b}$ | Ratio 24(OH)ase/Ca$^{2+}$ | Ratio 24(OH)ase/Ca$^{2+}$ increase |
|---|---|---|---|---|---|
| 3-day treatment | | | | | |
| vehicle | | 1 | 8.3 ± 0.5 | | |
| 1,25(OH)$_2$D$_3$ | 15 μg/kg | 5.7 | >15[c] | 0.38 | 0.85 |
| 4 | 10 mg/kg | 13.5 | 9.1 ± 0.5 | 1.48 | 16.9 |
| 4 | 30 mg/kg | 10.6 | 9.0 ± 0.6 | 1.18 | 15.1 |
| 7 | 100 μg/kg | 6.0 | 9.6 ± 0.5 | 0.63 | 5.17 |
| 7 | 500 μg/kg | 6.0 | 11.5 ± 0.9[c] | 0.52 | 1.88 |

TABLE 2-continued

Analysis of vitamin D target gene induction and serum calcium levels in mice treated with 1,25(OH)$_2$D$_3$, 4, or 7.

| Compound | Dose | Relative 24(OH)ase activity[a] | Serum Ca$^{2+}$[b] | Ratio 24(OH)ase/Ca$^{2+}$ | Ratio 24(OH)ase/Ca$^{2+}$ increase |
|---|---|---|---|---|---|
| 5-day treatment | | | | | |
| vehicle | | 1 | 8.6 ± 0.4 | | |
| 1,25(OH)$_2$D$_3$ | 2 µg/kg | 20.8 | 9.7 ± 0.6 | 2.14 | 18.9 |
| 1,25(OH)$_2$D$_3$ | 5 µg/kg | 24.9 | 10.5 ± 0.6[c] | 2.37 | 13.1 |
| 4 | 10 mg/kg | 30.8 | 9.1 ± 0.2 | 3.38 | 61.6 |
| 4 | 30 mg/kg | 53.7 | 10.1 ± 0.5 | 5.31 | 35.8 |

[a]Corrected with GAPDH; error within groups ~10%.
[b]Normal serum calcium ~7.9–10.5 mg/dL.
[c]Statistically different than vehicle (ANOVA, p < 0.01).

These results show that non-secosteroidal vitamin D3 mimics: 1) induce 24(OH)ase RNA, a known VDR target gene, and 2) have a superior ratio of vitamin D type activity relative to the undesirable elevation of serum calcium levels.

Example C

In vivo efficacy. Nude mice (6 weeks old) were housed under normal light and fed a vitamin D deficient, calcium replete diet (Purina Mills) for 7–10 days prior to injection with LNCaP cells. Tumors were allowed to grow 2–4 weeks prior to dosing. Compounds or vehicle were administered in sesame oil by oral gavage (0.1 mL dose volume). Dosing was daily for the extent of the study. Tumor measurements were taken on days 10 and 15. Animals were then euthanized, and kidneys and blood retrieved. Serum calcium measurements were taken from the final bleed and an intermediate bleed on day 10. FIG. 1 displays results for 3 mg/kg and 10 mg/kg of compound 4 vs vehicle in these experiments. As shown in FIG. 1a, mice treated with compound 4 showed decreased tumor growth rates as compared to the control group. FIG. 1b shows that hypercalcemia was not observed at these dosage levels of compound 4. Average animal weight change per group was as follows: Vehicle, −7.2%; Compound 4 (3 mg/kg), −2.1%; Compound 4 (10 mg/kg), −8.9%.

The foregoing examples are provided only to illustrate the present invention and are in no way intended to limit to the scope thereof. The skilled practitioner will understand that considerable variations in the practice of this invention are possible within the spirit and scope as claimed below.

We claim:
1. A compound of formula II:

II wherein:
X and Y are each independently selected from the group consisting of O, S, and NR$^7$;
Z is selected from the group consisting of C=O, CH(OR$^8$), and CH(NR$^9$R$^{10}$);

R$^1$ and R$^2$ are independently selected from the group consisting of alkyl groups, optionally fluorinated; or together R$^1$ and R$^2$ form a cycloalkylidene having 3 to 8 carbon atoms, optionally fluorinated;

R$^3$ and R$^4$ are independently selected from the group consisting of halogen; lower n-alkyl, optionally fluorinated; and lower alkoxy, optionally fluorinated;

R$^5$ is selected from the group consisting of H; optionally substituted alkyl groups; optionally substituted alkenyl groups; optionally substituted alkynyl groups; optionally substituted aryl groups; OR$^{11}$; NR$^{12}$R$^{13}$; or together with R$^8$, R$^9$, or R$^{10}$ forms a 3- to 12-membered cyclic group wherein said cyclic group is selected from the group consisting of amidines, amines, ethers, lactams, lactones, ketals, hemiketals, aminals, hemiaminals, carbonates, carbamates, ureas, and combinations thereof;

R$^6$ is selected from the group consisting of H and alkyl groups, optionally substituted;

R$^7$ is selected from the group consisting of H and alkyl groups, optionally substituted;

R$^8$ is selected from the group consisting of H, optionally substituted alkyl groups, optionally substituted alkenyl groups, optionally substituted alkynyl groups, optionally substituted aryl group, and optionally substituted acyl groups;

R$^9$ and R$^{10}$ are independently selected from the group consisting of H, optionally substituted alkyl groups, optionally substituted alkenyl groups, optionally substituted alkynyl groups, optionally substituted aryl groups, and optionally substituted acyl groups;

R$^{11}$ is selected from the group consisting of H, optionally substituted alkyl groups, optionally substituted alkenyl groups, optionally substituted alkynyl groups, optionally substituted aryl groups, and optionally substituted acyl groups; and R$^{12}$ and R$^{13}$ are independently selected from the group consisting of H, optionally substituted alkyl groups, optionally substituted alkenyl groups, optionally substituted alkynyl groups, optionally substituted aryl groups, and optionally substituted acyl groups and pharmaceutically acceptable salts thereof; with the provisos that:
a. when X and Y are both O, Z is C=O, and R$^5$ is selected from the group consisting of OH and C$_1$–C$_4$ alkoxy, then R$^6$ is not carboxymethyl and alkyl esters thereof;

b. when X and Y are both O, and Z is selected from the group consisting of CH(OR$^8$) and CH(NR$^9$R$^{10}$), then R$^5$ is not H or primary alkyl;
c. when X and Y are both O, and Z is CH(OR$^8$), then R$^6$ and R$^8$ do not both comprise aziridines;
d. when X and Y are both O, and Z is CH(OR$^8$), then R$^5$, R$^6$, and R$^8$ do not simultaneously comprise alkenyl ethers; and
e. when X and Y are both O, and Z is CH(OR$^8$), then R$^5$ and R$^6$ do not both comprise glycidyl ethers.

2. A compound of claim 1 wherein R$^3$ and R$^4$ are each methyl; X and Y are each O; and R$^5$ is t-butyl.

3. A compound of claim 2 wherein Z is C=O.

4. A compound of claim 2 wherein Z is CH(OH).

5. A compound of claim 3 wherein R$^1$ and R$^2$ are together cyclohexylidene.

6. A compound of claim 3 wherein R$^1$ and R$^2$ are each ethyl.

7. A compound of claim 4 wherein R$^1$ and R$^2$ are each ethyl.

8. The compound of claim 5 wherein R$^6$ is 2-oxo-3,3-dimethylbutyl.

9. The compound of claim 6 wherein R$^6$ is 2-oxo-3,3-dimethylbutyl.

10. The compound of claim 6 wherein R$^6$ is 2,3-epoxypropyl.

11. The compound of claim 6 wherein R$^6$ is 2-hydroxy-3,3-dimethylbutyl.

12. The compound of claim 7 wherein R$^6$ is 2-hydroxy-3,3-dimethylbutyl.

13. A method for the treatment or prophylaxis of disease states with abnormal calcium regulatory, abnormal immune responsive, hyperproliferative, and/or neurodegenerative characteristics in mammals comprising the administration of effective amounts of a compound of formula I:

wherein:
X and Y are each independently selected from the group consisting of O, S, and NR$^7$;
Z is selected from the group consisting of C=O, CH(OR$^8$), and CH(NR$^9$R$^{10}$);
R$^1$ and R$^2$ are independently selected from the group consisting of alkyl groups, optionally fluorinated; or together R$^1$ and R$^2$ form a cycloalkylidene having 3 to 8 carbon atoms, optionally fluorinated;
R$^3$ and R$^4$ are independently selected from the group consisting of halogen; lower n-alkyl, optionally fluorinated; and lower alkoxy, optionally fluorinated;
R$^5$ is selected from the group consisting of H; optionally substituted alkyl groups; optionally substituted alkenyl groups; optionally substituted alkynyl groups; optionally substituted aryl groups; OR$^{11}$; NR$^{12}$R$^{13}$; or together with R$^8$, R$^9$, or R$^{10}$ forms a 3- to 12-membered cyclic group wherein said cyclic group is selected from the group consisting of amidines, amines, ethers, lactams, lactones, ketals, hemiketals, aminals, hemiaminals, carbonates, carbamates, ureas, and combinations thereof;

R$^6$ is selected from the group consisting of H and alkyl groups, optionally substituted;
R$^7$ is selected from the group consisting of H and alkyl groups, optionally substituted;
R$^8$ is selected from the group consisting of H, optionally substituted alkyl groups, optionally substituted alkenyl groups, optionally substituted alkynyl groups, optionally substituted aryl group, and optionally substituted acyl groups;
R$^9$ and R$^{10}$ are independently selected from the group consisting of H, optionally substituted alkyl groups, optionally substituted alkenyl groups, optionally substituted alkynyl groups, optionally substituted aryl groups, and optionally substituted acyl groups;
R$^{11}$ is selected from the group consisting of H, optionally substituted alkyl groups, optionally substituted alkenyl groups, optionally substituted alkynyl groups, optionally substituted aryl groups, and optionally substituted acyl groups; and
R$^{12}$ and R$^{13}$ are independently selected from the group consisting of H, optionally substituted alkyl groups, optionally substituted alkenyl groups, optionally substituted alkynyl groups, optionally substituted aryl groups, and optionally substituted acyl groups and pharmaceutically acceptable salts thereof.

14. The method of claim 13 wherein the disease state is leukemia.

15. The method of claim 13 wherein the disease state is cancer.

16. The method of claim 13 wherein the disease state is psoriasis.

17. The method of claim 13 wherein the disease state is osteoporosis.

18. The method of claim 13 wherein the disease state is rheumatoid arthritis.

19. The method of claim 13 wherein the disease state is Alzheimer's disease.

20. The method of claim 13 wherein the disease state is an autoimmune condition.

21. The method of claim 13 wherein the disease state is a dermatological condition.

22. The method of claim 13 wherein the disease state is selected from the group consisting of renal osteodystrophy, renal failure, abnormal bone development, humoral hypercalcemia of malignancy, acne, alopecia, host-graft rejection, multiple sclerosis, autoimmune induced diabetes, and scleroderma.

23. A method for modulating of the vitamin D$_3$ receptor comprising the administration of effective amounts of a compound of formula I:

wherein:
X and Y are each independently selected from the group consisting of O, S, and NR$^7$;
Z is selected from the group consisting of C=O, CH(OR$^8$), and CH(NR$^9$R$^{10}$);

$R^1$ and $R^2$ are independently selected from the group consisting of alkyl groups, optionally fluorinated; or together $R^1$ and $R^2$ form a cycloalkylidene having 3 to 8 carbon atoms, optionally fluorinated;

$R^3$ and $R^4$ are independently selected from the group consisting of halogen; lower n-alkyl, optionally fluorinated; and lower alkoxy, optionally fluorinated;

$R^5$ is selected from the group consisting of H; optionally substituted alkyl groups; optionally substituted alkenyl groups; optionally substituted alkynyl groups; optionally substituted aryl groups; $OR^{11}$; $NR^{12}R^{13}$; or together with $R^8$, $R^9$, or $R^{10}$ forms a 3- to 12-membered cyclic group wherein said cyclic group is selected from the group consisting of amidines, amines, ethers, lactams, lactones, ketals, hemiketals, aminals, hemiaminals, carbonates, carbamates, ureas, and combinations thereof;

$R^6$ is selected from the group consisting of H and alkyl groups, optionally substituted;

$R^7$ is selected from the group consisting of H and alkyl groups, optionally substituted;

$R^8$ is selected from the group consisting of H, optionally substituted alkyl groups, optionally substituted alkenyl groups, optionally substituted alkynyl groups, optionally substituted aryl group, and optionally substituted acyl groups;

$R^9$ and $R^{10}$ are independently selected from the group consisting of H, optionally substituted alkyl groups, optionally substituted alkenyl groups, optionally substituted alkynyl groups, optionally substituted aryl groups, and optionally substituted acyl groups;

$R^{11}$ is selected from the group consisting of H, optionally substituted alkyl groups, optionally substituted alkenyl groups, optionally substituted alkynyl groups, optionally substituted aryl groups, and optionally substituted acyl groups; and $R^{12}$ and $R^{13}$ are independently selected from the group consisting of H, optionally substituted alkyl groups, optionally substituted alkenyl groups, optionally substituted alkynyl groups, optionally substituted aryl groups, and optionally substituted acyl groups and pharmaceutically acceptable salts thereof.

24. A method of activating transcription of a vitamin D target gene without significantly raising serum calcium levels by administering to an animal an effective amount of the non-secosteroidial vitamin D mimic of claim 1.

25. The method of claim 24 wherein said non-secosteroidal vitamin D mimic has a ratio of 24(OH)ase activity to serum calcium levels of at least 3.0.

26. The method of claim 24 wherein said non-secosteroidal vitamin D mimic is a compound of formula I:

I wherein:

X and Y are each independently selected from the group consisting of O, S, and $NR^7$;

Z is selected from the group consisting of C=O, $CH(OR^8)$, and $CH(R^9R^{10})$;

$R^1$ and $R^2$ are independently selected from the group consisting of alkyl groups, optionally fluorinated; or together $R^1$ and $R^2$ form a cycloalkylidene having 3 to 8 carbon atoms, optionally fluorinated;

$R^3$ and $R^4$ are independently selected from the group consisting of halogen; lower n-alkyl, optionally fluorinated; and lower alkoxy, optionally fluorinated;

$R^5$ is selected from the group consisting of H; optionally substituted alkyl groups; optionally substituted alkenyl groups; optionally substituted alkynyl groups; optionally substituted aryl groups; $OR^{11}$; $NR^{12}R^{13}$; or together with $R^8$, $R^9$, or $R^{10}$ forms a 3- to 12-membered cyclic group wherein said cyclic group is selected from the group consisting of amidines, amines, ethers, lactams, lactones, ketals, hemiketals, aminals, hemiaminals, carbonates, carbamates, ureas, and combinations thereof;

$R^6$ is selected from the group consisting of H and alkyl groups, optionally substituted;

$R^7$ is selected from the group consisting of H and alkyl groups, optionally substituted;

$R^8$ is selected from the group consisting of H, optionally substituted alkyl groups, optionally substituted alkenyl groups, optionally substituted alkynyl groups, optionally substituted aryl group, and optionally substituted acyl groups;

$R^9$ and $R^{10}$ are independently selected from the group consisting of H, optionally substituted alkyl groups, optionally substituted alkenyl groups, optionally substituted alkynyl groups, optionally substituted aryl groups, and optionally substituted acyl groups;

$R^{11}$ is selected from the group consisting of H, optionally substituted alkyl groups, optionally substituted alkenyl groups, optionally substituted alkynyl groups, optionally substituted aryl groups, and optionally substituted acyl groups; and $R^{12}$ and $R^{13}$ are independently selected from the group consisting of H, optionally substituted alkyl groups, optionally substituted alkenyl groups, optionally substituted alkynyl groups, optionally substituted aryl groups, and optionally substituted acyl groups and pharmaceutically acceptable salts thereof.

27. A pharmaceutical composition comprising:

wherein:

X and Y are each independently selected from the group consisting of O, S, and $NR^7$;

Z is selected from the group consisting of C=O, $CH(OR^8)$, and $CH(NR^9R^{10})$;

$R^1$ and $R^2$ are independently selected from the group consisting of alkyl groups, optionally fluorinated; or together $R^1$ and $R^2$ form a cycloalkylidene having 3 to 8 carbon atoms, optionally fluorinated;

$R^3$ and $R^4$ are independently selected from the group consisting of halogen; lower n-alkyl, optionally fluorinated; and lower alkoxy, optionally fluorinated;

R$^5$ is selected from the group consisting of H; optionally substituted alkyl groups; optionally substituted alkenyl groups; optionally substituted alkynyl groups; optionally substituted aryl groups; OR$^{11}$; NR$^{12}$R$^{13}$; or together with R$^8$, R$^9$, or R$^{10}$ forms a 3- to 12-membered cyclic group wherein said cyclic group is selected from the group consisting of amidines, amines, ethers, lactams, lactones, ketals, hemiketals, aminals, hemiaminals, carbonates, carbamates, ureas, and combinations thereof;

R$^6$ is selected from the group consisting of H and alkyl groups, optionally substituted;

R$^7$ is selected from the group consisting of H and alkyl groups, optionally substituted;

R$^8$ is selected from the group consisting of H, optionally substituted alkyl groups, optionally substituted alkenyl groups, optionally substituted alkynyl groups, optionally substituted aryl group, and optionally substituted acyl groups;

R$^9$ and R$^{10}$ are independently selected from the group consisting of H, optionally substituted alkyl groups, optionally substituted alkenyl groups, optionally substituted alkynyl groups, optionally substituted aryl groups, and optionally substituted acyl groups;

R$^{11}$ is selected from the group consisting of H, optionally substituted alkyl groups, optionally substituted alkenyl groups, optionally substituted alkynyl groups, optionally substituted aryl groups, and optionally substituted acyl groups; and R$^{12}$ and R$^{13}$ are independently selected from the group consisting of H, optionally substituted alkyl groups, optionally substituted alkenyl groups, optionally substituted alkynyl groups, optionally substituted aryl groups, and optionally substituted acyl groups and pharmaceutically acceptable excipients thereof;

with the provisos that:
 a. when X and Y are both O, Z is C=O, and R$^5$ is selected from the group consisting of OH and C$_1$–C$_4$ alkoxy, then R$^6$ is not carboxymethyl and alkyl esters thereof;
 b. when X and Y are both O, and Z is selected from the group consisting of CH(OR$^8$) and CH(NR$^9$R$^{10}$), then R$^5$ is not H or primary alkyl;
 c. when X and Y are both O, and Z is CH(OR$^8$), then R$^6$ and R$^8$ do not both comprise aziridines;
 d. when X and Y are both O, and Z is CH(OR$^8$), then R$^5$, R$^6$, and R$^8$ do not simultaneously comprise alkenyl ethers; and
 e. when X and Y are both O, and Z is CH(OR$^8$), then R$^5$ and R$^6$ do not both comprise glycidyl ethers.

28. A composition of claim 27 wherein R$^3$ and R$^4$ are each methyl; X and Y are each O; and R$^5$ is t-butyl.

29. A composition of claim 28 wherein Z is C=O.

30. A composition of claim 28 wherein Z is CH(OH).

31. A composition of claim 29 wherein R$^1$ and R$^2$ are together cyclohexylidene.

32. A composition of claim 29 wherein R$^1$ and R$^2$ are each ethyl.

33. A composition of claim 30 wherein R$^1$ and R$^2$ are each ethyl.

34. The composition of claim 31 wherein R$^6$ is 2-oxo-3,3-dimethylbutyl.

35. The composition of claim 32 wherein $^6$ is 2-oxo-3,3-dimethylbutyl.

36. The composition of claim 32 wherein R$^6$ is 2,3-epoxypropyl.

37. The composition of claim 32 wherein R$^6$ is 2-hydroxy-3,3-dimethylbutyl.

38. The composition of claim 33 wherein R$^6$ is 2-hydroxy-3,3-dimethylbutyl.

\* \* \* \* \*